US006861517B1

(12) United States Patent
Ueki

(10) Patent No.: US 6,861,517 B1
(45) Date of Patent: Mar. 1, 2005

(54) NUCLEIC ACID FRAGMENTS, RECOMBINANT VECTOR CONTAINING THE SAME AND METHOD FOR PROMOTING THE EXPRESSION OF STRUCTURAL GENE BY USING THE SAME

(75) Inventor: Jun Ueki, Sizuoka (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 09/600,602

(22) PCT Filed: Sep. 24, 1999

(86) PCT No.: PCT/JP99/05221

§ 371 (c)(1),
(2), (4) Date: Oct. 3, 2000

(87) PCT Pub. No.: WO00/31250

PCT Pub. Date: Jun. 2, 2000

(30) Foreign Application Priority Data

Nov. 19, 1998 (JP) .......................................... 10-329832

(51) Int. Cl.[7] .......................... C07H 21/04; C12N 15/82
(52) U.S. Cl. .................... 536/24.1; 536/23.1; 435/69.1; 435/320.1; 800/278; 800/295
(58) Field of Search ............................ 435/69.1, 320.1; 536/23.1, 24.1; 800/278, 295

(56) References Cited

U.S. PATENT DOCUMENTS

| 5,747,327 A | | 5/1998 | Ueki et al. ............... 435/252.3 |
| 5,801,016 A | * | 9/1998 | Morioka et al. |
| 5,973,226 A | | 10/1999 | Ueki et al. .................. 800/285 |
| 6,214,578 B1 | * | 4/2001 | Ueki et al. ................. 435/69.1 |

FOREIGN PATENT DOCUMENTS

| EP | 0 769 553 A1 | | 4/1997 |
| EP | 0846770 A1 | * | 6/1998 |
| WO | WO 93/19189 A1 | | 9/1993 |

OTHER PUBLICATIONS

Ueki et al (1999) Plant Cell Physiol. 40(6): 618–623.*
K.R. Luehrsen et al., Mol. Gen. Genet, vol. 225, No. 1, 1991, pp. 81–93.
C. Maas et al., Plant Molecular Biology, vol. 16, 1991, pp. 199–207.
C. Rathus et al., Plant Molecular Biology, vol. 23, 1993, pp. 613–618.
Desmond Mascarenhas et al., Plant Molecular Biology, vol. 15, 1990, pp. 913–920.
Maureen Clancy et al., Plant Science 98, 1994, pp. 151–161.

* cited by examiner

*Primary Examiner*—James Ketter
*Assistant Examiner*—David A. Lamberston
(74) *Attorney, Agent, or Firm*—Birch, Stewart, Kolasch & Birch, LLP

(57) ABSTRACT

Nucleic acid fragments having activities to prominently promote expression of structural genes located downstream thereof are disclosed. The nucleic acid fragment according to the present invention is an isolated nucleic acid fragment having the nucleotide sequence shown in SEQ ID NO: 1 in Sequence Listing or an isolated nucleic acid fragment (excluding the nucleic acid having the nucleotide sequence shown in SEQ ID NO: 3 in Sequence Listing) having the same nucleotide sequence as shown in SEQ ID NO: 1 except that one or a plurality of nucleotides are substituted or deleted, or except that one or a plurality of nucleotides are inserted or added, which has an activity to promote expression of a structural gene located downstream of said nucleic acid fragment.

5 Claims, No Drawings

US 6,861,517 B1

NUCLEIC ACID FRAGMENTS, RECOMBINANT VECTOR CONTAINING THE SAME AND METHOD FOR PROMOTING THE EXPRESSION OF STRUCTURAL GENE BY USING THE SAME

This application is the national phase under 35 U.S.C. § 371 of PCT International Application No. PCT/JP99/05221 which has an International filing date of Sep. 24, 1999, which designated the United States of America.

TECHNICAL FIELD

The present invention relates to a nucleic acid fragment having the function to promote expression of structural genes located downstream of the nucleic acid fragment, a recombinant vector containing the same and to a method for expression of structural genes using the same.

BACKGROUND ART

Promotion of expression of foreign genes is the most required technique for applying the genetic engineering techniques to plants. This technique includes utilization of a DNA fragment having an activity to promote gene expression. Known DNA fragments which promote expression of foreign genes include the intron of maize alcohol dehydrogenase (Callis et al. Gene & Development 1, 1183–1200 (1987)), and the first intron of rice phospholipase D (hereinafter also referred to as "PLD") (International Publication WO96/30510). Further, the influences on the activity to promote gene expression, by deleting a part of an internal region of an intron or by inserting the same intron into a site within the intron, have been reported (Mascarenhas et al. Plant Mol. Biol. 15, 913–920 (1990), Clancy et al. Plant Sci.98, 151–161 (1994)).

However, so far, the number of DNA fragments which may be used for this purpose is limited, and in most cases, their gene expression-promoting effects are insufficient. Therefore, a DNA fragment having higher activity has been demanded. Further, although it has been tried to increase the expression-promoting activity by modifying the intron sequences, the region having the activity to promote expression in an intron has not been reported, and a case wherein the promotion activity of an original intron-originated DNA fragment is doubled is not known.

DISCLOSURE OF THE INVENTION

Accordingly, an object of the present invention is to provide a novel nucleic acid fragment having a high activity to promote expression of structural genes located downstream of the nucleic acid fragment; a recombinant vector containing the above-mentioned nucleic acid fragment, in which expression of a structural gene is promoted; and to provide a method for promoting expression of a structural gene using the above-mentioned nucleic acid fragment, which structural gene is located downstream of the nucleic acid fragment.

The present inventor intensively studied to discover that a specific region in the first intron of rice phospholipase D (hereinafter also referred to as "PLD") has a high activity to promote gene expression, thereby completing the present invention.

That is, the present invention provides an isolated nucleic acid fragment having the nucleotide sequence shown in SEQ ID NO: 1 in Sequence Listing or an isolated nucleic acid fragment (excluding the nucleic acid having the nucleotide sequence shown in SEQ ID NO: 3 in Sequence Listing) having the same nucleotide sequence as shown in SEQ ID NO: 1 except that one or a plurality of nucleotides are substituted or deleted, or except that one or a plurality of nucleotides are inserted or added, which has an activity to promote expression of a structural gene located downstream of said nucleic acid fragment. The present invention also provides a recombinant vector comprising at least a nucleic acid fragment having the nucleotide sequence shown in SEQ ID NO: 1 in Sequence Listing or a nucleic acid fragment (excluding the nucleic acid having the nucleotide sequence shown in SEQ ID NO: 3 in Sequence Listing) having the same nucleotide sequence as shown in SEQ ID NO: 1 except that one or a plurality of nucleotides are substituted or deleted, or except that one or a plurality of nucleotides are inserted or added, which has an activity to promote expression of a structural gene located downstream of said nucleic acid fragment, and a structural gene located downstream of said nucleic acid fragment, whose expression is promoted by said nucleic acid fragment. The present invention further provides a method for promoting expression of a structural gene, comprising inserting, at a location upstream of said structural gene, a nucleic acid fragment having the nucleotide sequence shown in SEQ ID NO: 1 in Sequence Listing or a nucleic acid fragment (excluding the nucleic acid having the nucleotide sequence shown in SEQ ID NO: 3 in Sequence Listing) having the same nucleotide sequence as shown in SEQ ED NO: 1 except that one or a plurality of nucleotides are substituted or deleted, or except that one or a plurality of nucleotides are inserted or added, which has an activity to promote expression of a structural gene located downstream of said nucleic acid fragment. The present invention further provides a plant in which expression of a desired structural gene is promoted by the method according to the present invention as well as progenies thereof retaining the character.

By the present invention, a novel nucleic acid fragment which significantly promotes expression of a structural gene by inserting the nucleic acid into a site upstream of the structural gene was provided. By inserting the nucleic acid fragment according to the present invention into a site upstream of a structural gene, expression of the structural gene is promoted. Therefore, by the present invention, expression of; for example, a foreign gene in a recombinant vector may be promoted, so that it is expected that the present invention will largely contribute to the field of genetic engineering or the like.

BEST MODE FOR CARRYING OUT THE INVENTION

As mentioned above, the nucleic acid fragment according to the present invention is the nucleic acid fragment having the nucleotide sequence shown in SEQ ID NO: 1 in Sequence Listing or the nucleic acid fragment having the same nucleotide sequence as shown in SEQ ID NO: 1 except that one or a plurality of nucleotides are substituted or deleted, or except that one or a plurality of nucleotides are inserted or added, which has an activity to promote expression of a structural gene located downstream of the nucleic acid fragment. However, the nucleotide sequence shown in SEQ ID NO: 3 in Sequence Listing is the nucleotide sequence of the first intron of rice PLD, and since it has been disclosed by the present inventor that the first intron of rice PLD has an activity to promote expression of the gene located downstream thereof (International Publication WO96/30510), this sequence is excluded. The nucleotide sequence shown in SEQ ID NO:1 is the nucleotide sequence of the region in the first intron (SEQ ID NO: 3) of rice PLD from the second nucleotide (hereinafter indicated such as "2 nt") from the 5'-end to 65 nt.

As mentioned above, the nucleic acid fragments (hereinafter also referred to as "modified nucleic acid fragment" for convenience) having the same nucleotide sequence as shown in SEQ ID NO: 1 except that one or a plurality of nucleotides are substituted or deleted, or except that one or a plurality of nucleotides are inserted or added, which have activities to promote expression of a structural gene located downstream of said nucleic acid fragments are also within the scope of the present invention. In this case, the region in the modified nucleic acid fragment, which corresponds to a region in the sequence shown in SEQ ID NO: 1 preferably has a homology of not less than 70%, more preferably not less than 85%, more preferably not less than 95% with the sequence shown in SEQ ID NO: 1. Further, these modified nucleic acid fragments preferably hybridize with the nucleic acid having the nucleotide sequence shown in SEQ ID NO: 1 under stringent condition (i.e., hybridization is carried out in an ordinary hybridization solution such as 5× Denhardt's reagent, 6×SSC, 0.5% SDS or 0.1% SDS, at 50 to 65° C., preferably in two steps at 50° C. and at 60° C., or in four steps at 50° C., 55° C., 60° C. and 65° C.).

When inserting the nucleic acid according to the present invention into a site upstream of a structural gene of which expression is desired to be promoted, it is preferred to insert a fragment whose size is as small as possible, which fragment has an activity to promote gene expression. Thus, the number of nucleotides in the nucleic acid fragment according to the present invention is preferably not more than 120, more preferably not more than 80, and more preferably not more than 64.

By ligating two or more fragments according to the present invention, the activity may be increased. In this case, the nucleic acid fragments according to the present invention may be directly ligated or an intervening sequence may exist therebetween.

The nucleic acid according to the present invention may be either DNA or RNA. However, DNA is preferred in view of stability.

The nucleic acid fragments according to the present invention may easily be prepared by chemical synthesis. Alternatively, since the nucleotide sequence of the first intron of rice PLD gene is known (International Publication WO96/30510), the nucleic acid fragments according to the present invention may easily be obtained by nucleic acid amplification methods such as PCR using the genomic DNA of rice as a template. PCR is well-known in the art and a kit and apparatus therefor are commercially available, so that it can be easily carried out.

In cases where a plurality of nucleic acid fragments according to the present invention are ligated, a plurality of nucleic acid fragments according to the present invention may be preliminarily ligated, or a nucleic acid fragment according to the present invention may be inserted into a region containing the nucleic acid fragment according to the present invention.

By inserting the above-described nucleic acid fragment according to the present invention to a site upstream of a structural gene, the expression of the structural gene may be promoted. Structural genes are controlled by a promoter located upstream thereof. The nucleic acid fragment according to the present invention may be inserted either between the promoter and the structural gene or at a site upstream of the promoter, and the former is preferred. In this case, the distance between the nucleic acid fragment according to the present invention and the structural gene may preferably be 0 bp to 1000 bp, and the distance between the promoter and the nucleic acid fragment according to the present invention nay also preferably be 0 bp to 1000 bp.

It is preferred to insert the nucleic acid fragment according to the present invention into an intron sequence located upstream of the structural gene of which expression is to be promoted. Although such an intron sequence is not restricted, a preferred example is the first intron (SEQ ID NO: 3) of rice PLD gene. In cases where the nucleic acid fragment according to the present invention is inserted into an intron sequence, the site of insertion is not restricted. A part of a primer may be inserted together with an intron fragment. However, in cases where the intron is the first intron (SEQ ID NO: 3) of rice PLD gene, it is preferred to insert the nucleic acid fragments according to the present invention into the site of 1 nt or 65 nt so that a plurality of the nucleic acid fragments according to the present invention are ligated. It is especially preferred to insert the nucleic acid fragment according to the present invention into the site of 65 at so as to directly ligate two nucleic acid fragments according to the present invention. Although there are cases where an intron sequence does not exist upstream of the structural gene of which expression is to be promoted, in cases where an appropriate intron sequence does not exist, an appropriate intron sequence such as the first intron of rice PLD gene is firstly inserted to a site upstream of the structural gene of which expression is to be promoted, and then the nucleic acid fragment according to the present invention may be inserted therein. Insertion may easily be carried out by a conventional method using one or more restriction enzymes.

The present invention also provides recombinant vectors obtained by applying the above-described method of the present invention to an expression vector. The recombinant vector according to the present invention may easily be prepared by inserting the nucleic acid fragment according to the present invention and a structural gene of which expression is to be promoted into a cloning site of a commercially available expression vector. Such an expression vector may preferably be one for plant. Various expression vectors for plants are well-known in the art and commercially available. These expression vectors include a replication origin for replication in host cells, a promoter, cloning sites giving restriction sites for inserting foreign genes, and a selection marker such as a drug resistant gene, and usually contain a terminator which stably terminates transcription. In the method of the present invention, any of these known expression vectors may be employed.

EXAMPLES

The present invention will now be described more concretely by way of examples thereof. It should be noted that the examples are presented for the illustration purpose only and should net be interpreted in any restrictive way.

Into a vector pBI221 commercially available from CLONTECH, containing beta-Glucuronidase (GUS) gene downstream of 35S promoter (pBI221 (35S promoter, GUS)), a part of the inner region of the PLD intron, the PLD intron or the PLD intron plus a part of the PLD intron was inserted, and effect of promoting GUS expression was investigated.

The vectors were prepared by the following method. The first intron of rice PLD gene consists of 173 nucleotides (SEQ ID NO: 3). DNA fragments each of which corresponds to 2 nt–65 nt, 66 nt–120 nt or 121 nt–173 nt of the intron were prepared by PCR. The primers used were as follows: 5'-CTATGACCCGGGATCCTAAGCCCAGTGTGC-3' and (SEQ ID NO: 5) 5'-GCAAGCAAGCAGATCTGAGCGGAGAAGAAG-3'; (SEQ ID NO: 6) 5'-TATGACCCGGGATCCGATCTGCTTGCTTGC-3' and (SEQ ID NO: 7) 5'-ACCTAACGTAGATCTAGCGACACTCGCAGC-3'; (SEQ ID NO: 8) 5'-TATGACCCGGGATCCGCTTCGTCTTCCTTC-3' and, (SEQ ID NO. 9) 5'-GTGTCGCTAGATCTCTGCGCCCCCCCACAC-3', (SEQ ID NO. 10) Each of the PCR products was digested with restriction enzymes Barn HI and Bgl II, and then inserted into the Barn HI site in the multicloning site in pBI221 to obtain recombinant vectors (pBI[PLD(2-65)], pBI[PLD(66-120)] and pBI[PLD(121-173)]).

Further, vectors further containing the region of 2 nt–65 nt or 66 nt–120 nt of the PLD intron in addition to the PLD intron were prepared as follows: First, as described in WO96/30510, the first intron of rice PLD gene (SEQ ID NO: 3) was amplified by PCR using primers (5'-ACCCGGTAAGCCCAG-3',3'-(SEQ ID NO: 11) CCCCCGCGTCCATCC-5'), (SEQ ID NO: 12) and the amplified product was subcloned into pCRII vector. The resultant was digested with Eco RI and the cut out fragment was blunted with Klenow fragment, followed by inserting the blunted fragment into the Sma I site of pBI221 vector to obtain a vector (pBI[PLD]). The intron sequence was cut at its 65 nt with Bgl II, and the above-mentioned PCR product digested with Barn HI and Bgl II was inserted thereinto to obtain vectors (pBI[PLD+PLD(2-65)] and pBI[PLD+PLD (66-120)].

By the reported method (Shimamoto et al. Nature, 338, 274–276 (1989)), each of the above-described recombinant vectors was introduced into rice cultured cells (Baba et al. Plant Cell Physiol. 27,463–471 (1986)), and β-glucuronidase (GUS) activity was measured. The relative activities are shown in Table 1.

TABLE 1

| Vector | Relative GUS Activity |
| --- | --- |
| pBI221 | 1.0 |
| pBI[PLD] | 14 |
| pBI[PLD(2–65)] | 4.9 |
| pBI[PLD(66–120)] | 2.5 |
| pBI[PLD(121–173)] | 1.7 |
| pBI[PLD + PLD(2–65)] | 28 |
| pBI[PLD + PLD(66–120)] | 14 |

All of the three regions which are the parts of the PLD intron exhibited GUS activities higher than that of the control (pBI221). The region of 2 nt–65 at showed the highest activity and the region of 66 nt–120 at showed the second highest activity. As for the cases where each of these two regions was inserted into the intron, the activity was twice of the original activity attained by the intron alone in the case of inserting the region of 2 nt–65 nt into the intron, while the activity was not increased when the region of 66 nt–120 nt was inserted.

These results revealed that the region of 2 nt–65 nt of the PLD intron has an activity to promote gene expression. The nucleotide sequence of the region of 2 nt–65 nt is shown in SEQ ID NO: 1, the nucleotide sequence (containing 10 nucleotides each at the both ends) of the intron into which the region of 2 nt–65 nt is further inserted is shown in SEQ ID NO:4, and the nucleotide sequence in which the exon sequences at the both ends are removed is shown in SEQ ID NO: 2.

What is claimed is:

1. An isolated nucleic acid no more than 120 nucleotides in length and comprising the nucleotide sequence shown in SEQ ID NO: 1 and that hybridizes to a polynucleotide having a sequence that is the complement of SEQ ID NO: 3 under conditions equivalent to 5× Denhardt's solution, 6×SSC, 0.5% to 0.1% SDS, at a temperature from 50 to 65° C., and which has activity to promote expression in a cell of a structural gene located downstream of said nucleic acid.

2. The nucleic acid according to claim 1, consisting of a polynucleotide having the sequence of SEQ ID NO: 1.

3. A nucleic acid comprising a plurality of nucleic acids according to claim 1 or 2 that are ligated.

4. A plant, or progeny thereof, comprising a recombinant vector comprising a nucleic acid no more than 120 nucleotides in length and comprising the nucleotide sequence shown in SEQ ID NO: 1 that hybridizes to a polynucleotide having a sequence that is the complement of SEQ ID NO: 3 under conditions equivalent to 5× Denhardt's solution, 6×SSC, 0.5% to 0.1% SDS, at a temperature from 50 to 65° C., and which has activity to promote expression in a cell of a structural gene located downstream of said nucleic acid and a structural gene located downstream of said nucleic acid whose expression in a cell is promoted by said nucleic acid.

5. A plant, or progeny thereof, comprising at least one polynucleotide no more than 120 nucleotides in length and comprising the nucleotide sequence shown in SEQ ID NO: 1 that hybridizes to a polynucleotide having a sequence that is the complement of SEQ ID NO: 3 under conditions equivalent 5× Denhardt's solution, 6×SSC, 0.5% to 0.1% SDS, at a temperature from 50 to 65° C., and which has activity to promote expression of a structural gene located downstream of said nucleic acid, wherein said at least one polynucleotide is inserted into an intron of a structural gene.

* * * * *

SEQUENCE LISTING

<160> NUMBER OF SEQ ID NOS: 12

<210> SEQ ID NO 1
<211> LENGTH: 64
<212> TYPE: DNA
<213> ORGANISM: Oryza sativa

<400> SEQUENCE: 1

```
taagcccagt gtgcttaggc taagcgcact agagcttctt gctcgcttgc ttcttctccg    60
ctca                                                                 64
```

<210> SEQ ID NO 2
<211> LENGTH: 242
<212> TYPE: DNA
<213> ORGANISM: Oryza sativa

<400> SEQUENCE: 2

```
gtaagcccag tgtgcttagg ctaagcgcac tagagcttct tgctcgcttg cttcttctcc    60
gctcagatcc taagcccagt gtgcttaggc taagcgcact agagcttctt gctcgcttgc   120
ttcttctccg ctcagatctg cttgcttgct tgcttcgcta gaaccctact ctgtgctgcg   180
agtgtcgctg cttcgtcttc cttcctcaag ttcgatctga ttgtgtgtgt ggggggggcgc   240 ag                                                                  242
```

<210> SEQ ID NO 3
<211> LENGTH: 173
<212> TYPE: DNA
<213> ORGANISM: Oryza sativa

<400> SEQUENCE: 3

```
gtaagcccag tgtgcttagg ctaagcgcac tagagcttct tgctcgcttg cttcttctcc      60
gctcagatct gcttgcttgc ttgcttcgct agaaccctac tctgtgctgc gagtgtcgct     120
gcttcgtctt ccttcctcaa gttcgatctg attgtgtgtg tggggggggcg cag            173
```

<210> SEQ ID NO 4
<211> LENGTH: 262
<212> TYPE: DNA
<213> ORGANISM: Oryza sativa

<400> SEQUENCE: 4

```
tcaccacccg gtaagcccag tgtgcttagg ctaagcgcac tagagcttct tgctcgcttg      60
cttcttctcc gctcagatcc taagcccagt gtgcttaggc taagcgcact agagcttctt     120
gctcgcttgc ttcttctccg ctcagatctg cttgcttgct tgcttcgcta gaaccctact     180
ctgtgctgcg agtgtcgctg cttcgtcttc cttcctcaag ttcgatctga ttgtgtgtgt     240
ggggggcgc aggtagggcg ag                                                262
```

<210> SEQ ID NO 5
<211> LENGTH: 30
<212> TYPE: DNA
<213> ORGANISM: Oryza sativa

<400> SEQUENCE: 5

```
ctatgacccg ggatcctaag cccagtgtgc                                        30
```

<210> SEQ ID NO 6
<211> LENGTH: 30
<212> TYPE: DNA
<213> ORGANISM: Oryza sativa

<400> SEQUENCE: 6

```
gcaagcaagc agatctgagc ggagaagaag                                        30
```

<210> SEQ ID NO 7
<211> LENGTH: 30
<212> TYPE: DNA
<213> ORGANISM: Oryza sativa

<400> SEQUENCE: 7

```
tatgacccgg gatccgatct gcttgcttgc                                        30
```

<210> SEQ ID NO 8
<211> LENGTH: 30
<212> TYPE: DNA
<213> ORGANISM: Oryza sativa

<400> SEQUENCE: 8

```
acctaacgta gatctagcga cactcgcagc                                        30
```

<210> SEQ ID NO 9
<211> LENGTH: 30
<212> TYPE: DNA
<213> ORGANISM: Oryza sativa

```
<400> SEQUENCE: 9
tatgacccgg gatccgcttc gtcttccttc                              30

<210> SEQ ID NO 10
<211> LENGTH: 30
<212> TYPE: DNA
<213> ORGANISM: Oryza sativa

<400> SEQUENCE: 10
gtgtcgctag atctctgcgc cccccacac                               30

<210> SEQ ID NO 11
<211> LENGTH: 15
<212> TYPE: DNA
<213> ORGANISM: Oryza sativa

<400> SEQUENCE: 11
acccggtaag cccag                                              15

<210> SEQ ID NO 12
<211> LENGTH: 15
<212> TYPE: DNA
<213> ORGANISM: Oryza sativa

<400> SEQUENCE: 12
cccccgcgtc catcc                                              15
```